(12) United States Patent
Echt et al.

(10) Patent No.: US 7,702,392 B2
(45) Date of Patent: Apr. 20, 2010

(54) METHODS AND APPARATUS FOR DETERMINING CARDIAC STIMULATION SITES USING HEMODYNAMIC DATA

(75) Inventors: Debra S. Echt, Woodside, CA (US); Richard E. Riley, Palo Alto, CA (US); Mark W. Cowan, Fremont, CA (US); Axel F. Brisken, Fremont, CA (US)

(73) Assignee: EBR Systems, Inc., Sunnyvale, CA (US)

( * ) Notice: Subject to any disclaimer, the term of this patent is extended or adjusted under 35 U.S.C. 154(b) by 623 days.

(21) Appl. No.: 11/351,569

(22) Filed: Feb. 10, 2006

(65) Prior Publication Data
US 2007/0060961 A1 Mar. 15, 2007

Related U.S. Application Data

(60) Provisional application No. 60/716,202, filed on Sep. 12, 2005.

(51) Int. Cl.
*A61N 1/00* (2006.01)
(52) U.S. Cl. .................................................. 607/27
(58) Field of Classification Search ............... 607/4–28
See application file for complete search history.

(56) References Cited

U.S. PATENT DOCUMENTS

| | | |
|---|---|---|
| 3,659,615 A | 5/1972 | Enger |
| 3,693,627 A | 9/1972 | Berkovits |
| 3,698,398 A | 10/1972 | Berkovits |
| 3,735,756 A | 5/1973 | Richards et al. |
| 3,832,994 A | 9/1974 | Bicher et al. |
| 3,857,382 A | 12/1974 | Williams, Jr. et al. |
| 3,939,844 A | 2/1976 | Pequignot |
| 3,942,534 A | 3/1976 | Allen et al. |
| 4,181,133 A | 1/1980 | Kolenik et al. |
| 4,256,115 A | 3/1981 | Bilitch |
| 4,265,228 A | 5/1981 | Zoll |
| 4,280,502 A | 7/1981 | Baker, Jr. et al. |
| 4,561,442 A | 12/1985 | Vollmann et al. |

(Continued)

FOREIGN PATENT DOCUMENTS

| | | |
|---|---|---|
| DE | 4330680 | 3/1995 |
| WO | WO-9961058 | 12/1999 |
| WO | WO-03070323 | 8/2003 |

OTHER PUBLICATIONS

International Search Report and Written Opinion for Application No. PCT/US2006/035346, Apr. 27, 2007, 5 pages.

(Continued)

*Primary Examiner*—Scott M Getzow
(74) *Attorney, Agent, or Firm*—Townsend and Townsend and Crew LLP

(57) ABSTRACT

Methods and apparatus for determining an endocardial implantation site for implanting an electrode, such as a leadless stimulation electrode. An embodiment of one method in accordance with the invention includes delivering sufficient electrical energy for initiation of cardiac activation to a plurality of different test locations at the heart of a patient, and determining hemodynamic responses in reaction to that the stimulus delivered to the different test locations. This method further includes identifying an implantation site for implanting the electrode by selecting at least one of the test locations corresponding to a favorable hemodynamic response.

11 Claims, 5 Drawing Sheets

U.S. PATENT DOCUMENTS

| | | | |
|---|---|---|---|
| 4,577,633 A | 3/1986 | Berkovits et al. |
| 4,651,716 A | 3/1987 | Forester et al. |
| 4,690,144 A | 9/1987 | Rise et al. |
| 4,830,006 A | 5/1989 | Haluska et al. |
| 5,018,523 A | 5/1991 | Bach, Jr. et al. |
| 5,063,928 A | 11/1991 | Grevis et al. |
| 5,103,129 A | 4/1992 | Slayton et al. |
| 5,113,859 A | 5/1992 | Funke |
| 5,165,403 A | 11/1992 | Mehra |
| 5,170,784 A | 12/1992 | Ramon et al. |
| 5,174,289 A | 12/1992 | Cohen |
| 5,193,539 A | 3/1993 | Schulman et al. |
| 5,292,338 A | 3/1994 | Bardy |
| 5,377,166 A | 12/1994 | Kuhn |
| 5,405,367 A | 4/1995 | Schulman et al. |
| 5,411,535 A | 5/1995 | Fujii et al. |
| 5,433,731 A | 7/1995 | Hoegnelid et al. |
| 5,674,251 A | 10/1997 | Combs et al. |
| 5,749,909 A | 5/1998 | Schroeppel et al. |
| 5,751,539 A | 5/1998 | Stevenson et al. |
| 5,757,104 A | 5/1998 | Getman et al. |
| 5,766,227 A | 6/1998 | Nappholz et al. |
| 5,800,464 A | 9/1998 | Kieval |
| 5,814,089 A | 9/1998 | Stokes et al. |
| 5,817,130 A | 10/1998 | Cox et al. |
| 5,844,349 A | 12/1998 | Oakley et al. |
| 5,871,506 A | 2/1999 | Mower |
| 5,935,158 A | 8/1999 | Holmstrom et al. |
| 5,978,204 A | 11/1999 | Stevenson |
| 5,998,910 A | 12/1999 | Park et al. |
| 6,037,704 A | 3/2000 | Welle |
| 6,070,101 A | 5/2000 | Struble et al. |
| 6,078,837 A | 6/2000 | Peterson et al. |
| 6,110,098 A | 8/2000 | Renirie et al. |
| 6,223,079 B1 | 4/2001 | Bakels et al. |
| 6,233,484 B1 | 5/2001 | Ben-Haim et al. |
| 6,330,475 B1 | 12/2001 | Renirie et al. |
| 6,366,816 B1 | 4/2002 | Marchesi |
| 6,408,205 B1 | 6/2002 | Renirie et al. |
| 6,424,234 B1 | 7/2002 | Stevenson |
| 6,439,236 B1 | 8/2002 | Porter et al. |
| 6,445,953 B1 | 9/2002 | Bulkes et al. |
| 6,527,729 B1 | 3/2003 | Turcott |
| 6,534,895 B2 | 3/2003 | Kadota et al. |
| RE38,119 E | 5/2003 | Mower |
| 6,628,989 B1 | 9/2003 | Penner et al. |
| 6,645,145 B1 | 11/2003 | Dreschel et al. |
| 6,647,292 B1 | 11/2003 | Bardy et al. |
| 6,654,638 B1 | 11/2003 | Sweeney |
| 6,671,547 B2 | 12/2003 | Lyster et al. |
| 6,707,230 B2 | 3/2004 | Smith et al. |
| 6,721,597 B1 | 4/2004 | Bardy et al. |
| 6,728,576 B2 | 4/2004 | Thompson et al. |
| 6,754,528 B2 | 6/2004 | Bardy et al. |
| 6,754,531 B1 | 6/2004 | Kroll et al. |
| 6,764,446 B2 | 7/2004 | Wolinsky et al. |
| 6,788,974 B2 | 9/2004 | Bardy et al. |
| 6,834,204 B2 | 12/2004 | Ostroff et al. |
| 6,856,835 B2 | 2/2005 | Bardy et al. |
| 6,970,742 B2 | 11/2005 | Mann et al. |
| 7,010,350 B2 | 3/2006 | Kralik |
| 7,043,292 B2 | 5/2006 | Tarjan et al. |
| 7,283,874 B2 | 10/2007 | Penner |
| 7,349,740 B2 | 3/2008 | Soykan et al. |
| 2002/0077673 A1 | 6/2002 | Penner et al. |
| 2002/0087089 A1 | 7/2002 | Ben-Haim |
| 2003/0013974 A1 | 1/2003 | Natarajan et al. |
| 2003/0069625 A1 | 4/2003 | Ley et al. |
| 2004/0015104 A1 | 1/2004 | Goldberger |
| 2004/0167580 A1 | 8/2004 | Mann et al. |
| 2004/0172083 A1 | 9/2004 | Penner |
| 2004/0204744 A1 | 10/2004 | Penner et al. |
| 2004/0260346 A1 | 12/2004 | Overall et al. |
| 2006/0009831 A1 | 1/2006 | Lau et al. |
| 2006/0136004 A1 | 6/2006 | Cowan et al. |
| 2006/0224067 A1 | 10/2006 | Giftakis et al. |
| 2006/0241701 A1 | 10/2006 | Markowitz et al. |
| 2007/0032749 A1 | 2/2007 | Overall et al. |
| 2007/0232936 A1 | 10/2007 | Mann et al. |
| 2007/0260286 A1 | 11/2007 | Giftakis et al. |
| 2007/0265677 A1 | 11/2007 | Giftakis et al. |

OTHER PUBLICATIONS

Abraham et al., "Cardiac Resynchronization in Chronic Heart Failure for the MIRACLE study group", N Engl J Med, 2002, pp. 1845-1853, 346.

Allessie et al., "Regional Control of Atrial Fibrillation by Rapid Pacing in Conscious Dogs", Circulation, 1991, pp. 1689-1697, 84.

Ansalone et al., "Bi-ventricular Pacing I Heart Failure:Back to Basics in the Pathophysiology of Left Bundle Branch Block to Reduce the Number of Nonresponders", Am J Cardiol, 2003, pp. 55F-61F, 91.

Auricchio et al., "Cardiac Resynchronization Therapy: Current State of the Art", Circulation, 2004, pp. 300-307, 109.

Bardy et al., "The Totally Subcutaneous ICD System (The S-ICD)", PACE, 2002, pp. 578, 24.

Becker et al., "Suppression of Atrial Fibrillation by Multisite and Septa! Pacing in a Novel Experimental Model", Cardiovascular Research, 2001, pp. 476-481, 54(2).

Bradley D.J., et al., "Cardiac Resynchronization and Death from Progressive Heart Failure: A Meta Analysis of Randomized Controlled Trials", JAMA, 2003, pp. 730-740, 289.

Camm et al., Chapter 6: Nonpharmaceutical treatment of atrial fibrillation, 1994, pp. 125-147, vol. 76—Issue 1, Futura Publishing Company, Inc. Armonk, NY.

Dalecki et al., "Effects of Pulsed Ultrasound on the Frog Heart: I. Thresholds for Changes in Cardiac Rhythm and Aortic Pressure", Ultrasound in Med. and Biol., 1993, pp. 385-390, 19.

Dalecki et al., "Thresholds for premature ventricular contractions in frog hearts exposed to lithotripter fields", Ultrasound in Med. and Biol., 1991, pp. 341-346, 17.

Dalecki et al., Effects of Pulsed Ultrasound on the Frog Heart: II. An Investigation of Heating as a Potential Mechanism, Ultrasound in Med. and Biol., 1993, pp. 391-398, 19.

Daoud et al., "Implantation Techniques and Chronic Lead Parameters of Biventricular Pacing Dual-chamber Defibrillators", J Cardiovasc Electrophysiology, 2002, pp. 964-970, 13.

Daubert et al., "Permanent Left Ventricular Pacing With Transvenous Leads Inserted Into The Coronary Veins", PACE, 1998, pp. 239-245, 21.

Daubert et al., "Use of Specifically Designed Coronary Sinus Leads for Permanent Left as Ventricular Pacing: Preliminary Experience. II-NASPE", Abstract 17, PACE, 1997, pp. 20, vol. 76—Issue 1.

David Trial Investigators, "The Dual Chamber and WI Implantable Defibrillator (DAVID) Trial", JAMA, 2002, pp. 3115-3123, 288.

Deshmukh et al., "Direct His-bundle pacing: present and future", PACE, 2004, pp. 862-870, 27 [Pt.II].

Ellenbogen et al., "Detection and Management of An Implantable Cardioverter Defibrillator Lead Failure", JACC, 2003, pp. 73-80, 41.

Feldman et al., "Comparison of medical therapy, resynchronization and defibrillation therapies in heart failure trial (Companion)", Presented at ACC 2003 Late Breaking Clinical Trials, The Journal of Bone and Joint Surgery, 1 page, vol. 76—Issue 1.

Franz M.R., "Mechano-electrical feedback in ventricular myocardium", Cardiovascular Research, 1996, pp. 15-24, 32.

Gregoratos et al., "ACC/AHA/NASPE 2002 guideline update for implantation of cardiac pacemakers and antiarrhythmia devices", a report of the American College of Cardiology/American Heart Association Task Force on Practice Guidelines.ACC/AHA/NASPE Committee to Update the 1998 P, Circulation, 2002, pp. 2145-2161, 106.

Hu et al., "Stretch-Activated Ion Channels in the Heart", J. MoL Cell Cardiol, 1997, pp. 1511-1523, 29.

Hunt et al., "Evaluation and Management of Chronic Heart Failure in the Adult ACC/AHA Task Force on Practice Guidelines", JACC, 2002, pp. 2101-2113, 38.

International Search Report and Written Opinion of PCT Application No. PCT/US05/46532, dated Jun. 23, 2008, 8 pages total.

International Search Report and Written Opinion of PCT Application No. PCT/US2007/076812, mailed Apr. 7, 2008, 8 pages total.

Johnson et al., Adaptive Pacing During Ventricular Fibrillation, PACE, 2003, pp. 1824-1836, 26.

Kalman J.M., et al., "Regional Entrainment of Atrial Fibrillation in Man", J Cardiovasc Electrophysiol, 1991, pp. 867-876, 7.

Kass et al., "Improved Left Ventricular Mechanics from Acute VDD Pacing in Patients with Dilated Cardiomyopathy and Ventricular Conduction Delay", Circulation, 1999, pp. 1567-1573, 99.

Kenknight B.H., et al., "Regional Capture of Fibrillating Ventricular Myocardium", Circ Res, 1999, pp. 849-855, 77.

Kohl et al., "Stretch-induced changes in heart rate and rhythm: clinical observations, experiments and mathematical models", Progress in Biophysics and Molecular Biology, 1999, pp. 91-138, 71.

Kohl et al., "Sudden Cardiac Death by Commotio Cordis: Role of Mechano-Electrical Feedback", Cardiovascular Research, 2001, pp. 280-289, 50.

Leclercq C., et al., "Systolic Improvement and Mechanical Resynchronization does not Require Electrical Synchrony in the Dilated Failing Heart with Left Bundle-Branch Block", Circulation, 2002, pp. 1760-1763, 106.

Leclercq et al., "Is Dual Site Better than Single Site Atrial Pacing in the Prevention of Atrial Fibrillation?", PACE, 2000, pp. 2102-2107, 23.

Leclercq et al., "Acute Hemodynamic Effects of Biventricular DDD Pacing in Patients with End-Stage Heart Failure", JACC, 1998, pp. 1825-1831, 32.

Lee et al., "Effect of Implantable Defibrillators of Arrhythmic Events and Mortality in the Multicenter Unsustained Tachycardia Trial", Circulation., 2002, pp. 233-238, 106.

Linde et al., "Long-Term Benefits of Biventricular Pacing in Congestive Heart Failure: From the Multisite Stimulation in Cardiomyopathy (MUSTIC) Study", J Am Coll Cardiol, 2002, pp. 111-118, 40.

Miracle Trial Investigators, "Combined Cardiac Resynchronization and Implantable Cardioversion Defibrillation in Advanced Heart Failure: the Miracle ICD Trial", JAMA, 2003, pp. 2685-2694, 289.

Mirza et al., "Biatrial Pacing for Paroxysmal Atrial Fibrillation", J Am Coll Cardiol, 2002, pp. 457-463, 40.

Moss et al., "Prophylactic Implantation of a Defibrillator in Patients with Myocardial Infarction and Reduced Ejection Fraction", N Engl J Med., 2002, pp. 877-933, 346.

Niehaus et al., Non-Contact Cardiac Stimulation with focused Ultrasound Pulses, PACE, 2003, pp. 1023, 26.

Nielsen et al., "A Randomized Comparison of Atrial and Dual-Chambered Pacing in 177 Consecutive Patients With Sick Sinus Syndrome", J Am Coll Cardiol, 2003, pp. 614-623, 42.

Nolte et al., "Mechanically Induced Ventricular Extrasystoles in the Isolated Perfused Guinea-Pig Heart", Arzneim.-Forsch/Drug Research., 1987, pp. 1025-1029, 37(11).

Peschar et al., "Left Ventricular Septal and Apex Pacing for Optimal Pump Function in Canine Hearts", J Am Coll Cardiol, 2003, pp. 1218-1226, 41.

Reiter et al., "Effects of Mechano-Electrical Feedback: Potential Arrhythmogenic Influence in Patients With Congestive Heart Failure", Cardiovascular Research, 1996, pp. 44-51, 32.

Smailys et al., "Investigation of the Possibilities of cardiac Defibrillation by Ultrasound", Resuscitation, 1981, pp. 233-242, 9.

Sowton, "Clinical Results with the Tachylog Antitachycardia Pacemaker", PACE, 1984, pp. 1313-1317, 7(Part II).

Tacker W.A., "Fibrillation causes and criteria for defibrillation. In Defibrillation of the heart", The Journal of Bone and Joint Surgery, 1994, pp. 1-14, vol. 76—Issue 1, Tacker, WA, ed. Mosby-Year Book, Inc., St. Louis, Missouri.

The Antiarrhythmics Versus Implantable Defibrillators (AVID) Investigators,"A Comparison of Antiarrhythmic Drug Therapy with Implantable Defibrillators in Patients Resuscitated from Near Fatal Ventricular Arrhythmias", N Engl J Med, 1997, pp. 1576-1583, 337.

Valls-Bertault et al., "Adverse Events with Transvenous Left Ventricular Pacing in Patients with Severe Heart Failure: Early Experience from a Single Centre", Europace, 2001, pp. 60-63, 3.

Warren et al., "Clinical Evaluation of Automatic Tachycardia Diagnosis by an Implanted Device", PACE, 1986, pp. 1079-1083, 9 (Part II).

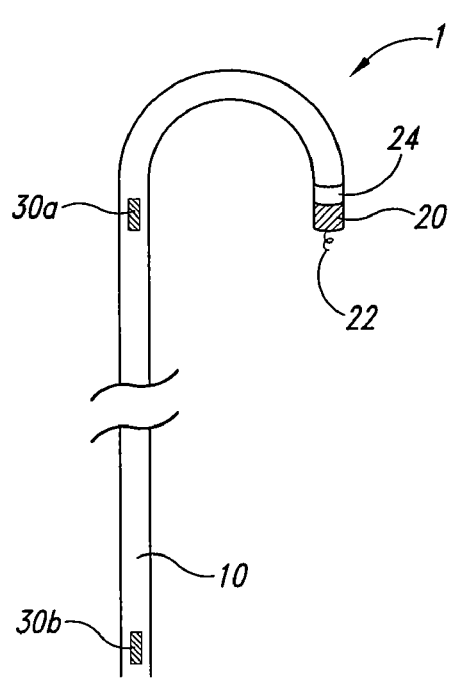
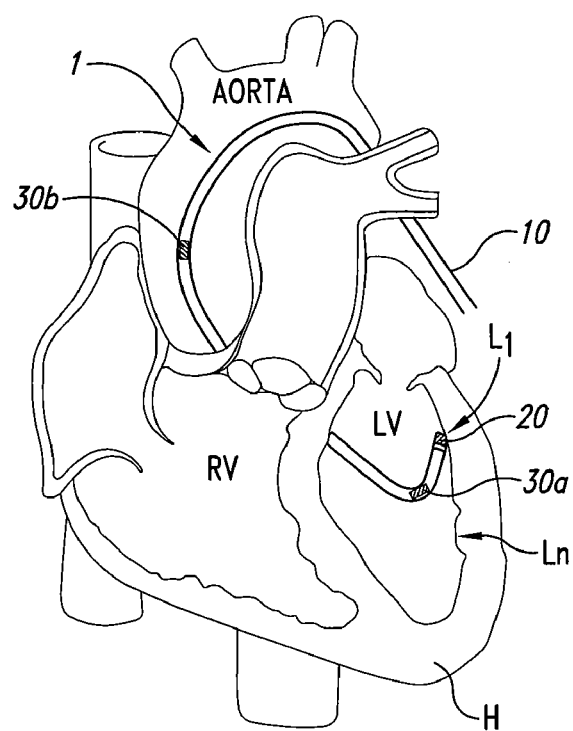
Fig. 1A    Fig. 1B
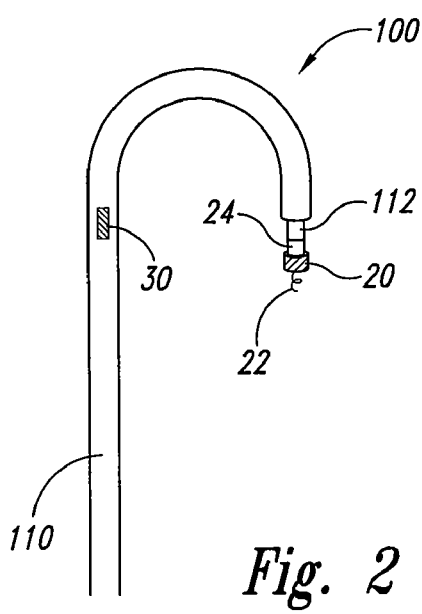
Fig. 2

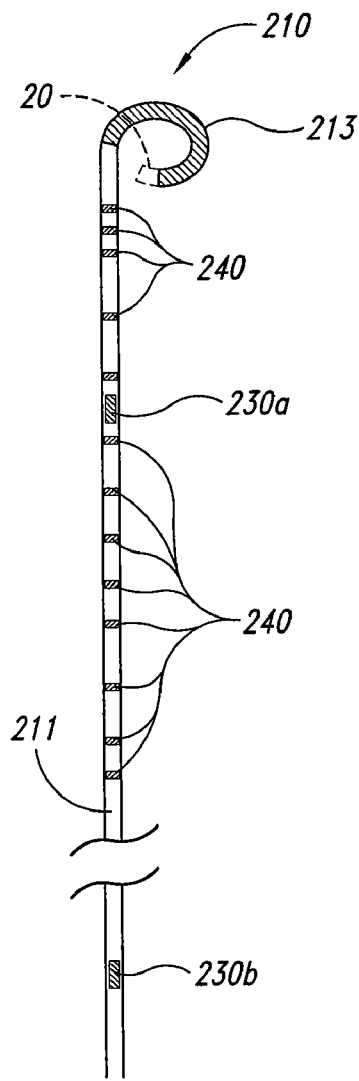
Fig. 3A
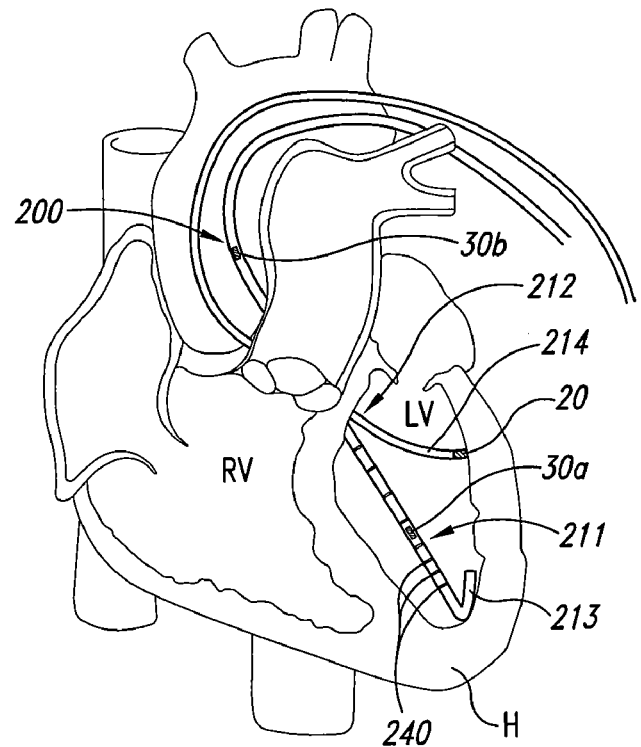
Fig. 3B
Fig. 3C

METHODS AND APPARATUS FOR DETERMINING CARDIAC STIMULATION SITES USING HEMODYNAMIC DATA

CROSS-REFERENCE TO RELATED APPLICATION

This application claims the benefit of U.S. Provisional Application No. 60/716,202, filed on Sep. 12, 2005, which is herein incorporated by reference.

TECHNICAL FIELD

The present invention relates generally to medical devices and methods for treating cardiac conditions. Several embodiments of the present invention are methods and apparatus for determining an implantation site or stimulation site within a heart chamber based on hemodynamic measurements.

BACKGROUND

Pacemakers and implantable cardioverters/defibrillators are widely used to treat a number of different cardiac conditions. For example, localized pacing has been used to terminate and/or control bradycardia, bradyarrhythmia, tachycardia, tachyarrhythmia, and other conditions. Over the years, many sophisticated algorithms and complex electromechanical devices have been developed and implemented in pacemaker technology for detecting the onset of abnormal rhythms and treating these conditions.

To better understand the effect of pacing devices, it is useful to understand the electrical-mechanical operation of the heart. The normal electrical activation system of the heart initiates left and right heart conduction using a complex structure/network of cardiac cells that rapidly conduct cellular-level electrical activation through cardiac tissue. For example, in the left and right ventricles of the heart, the Purkinje system, a specialized network of cells, conducts electrical activation endocardially and spreads the activation through the myocardial layers to the epicardium. Via connection to the atrial-ventricular node (A-V node), which is a specialized network of cells between the atria and the ventricles, normal ventricular electrical activation originates in the superior, septal aspect of the left ventricle, and then propagates through the septal wall, left ventricular free wall, and right ventricular free wall. This electrical activation induces the mechanical contractions of the ventricles that eject blood from the heart and into the vascular system. The strength and pattern of the mechanical contractility of the heart significantly affects the hemodynamic function. For example, when the normal electrical conduction pattern is blocked by ischemic regions in the ventricles, the mechanical contraction patterns of the heart are modified. Therefore, changes in the electrical conduction pattern have a direct impact on the hemodynamic function of the heart.

In the presence of cardiac disease, the dynamic and complex changes in regional electrical conduction and in mechanical function can lead to inefficiencies and cardiac hemodynamic output that eventually cause cardiomyopathy, mitral valve regurgitation, and other global physical and functional changes. Such mechanical dysfunction leads to further electrical conduction abnormalities, and thus further mechanical dysfunction. This progressively deleterious cycle of events leads to further inefficiencies and ever-worsening cardiovascular status (e.g., progressive heart failure).

Typical pacing devices artificially initiate electrical conduction in the heart by delivering small amounts of electrical current (e.g., a stimulation pulse) between two electrical contacts (electrodes) located on a lead placed in or on the heart. At least one electrode typically touches cardiac tissue. The site of the electrical contact then becomes the earliest site of activation and a conduction pattern propagates from this site throughout the cardiac tissue. It is desirable for pacing devices to deliver the stimulation pulse to a selected site along the normal electrical conduction paths in order to more appropriately synchronize the activation pattern of the heart. In many applications, for example, it would be desirable to stimulate from an endocardial location in the left ventricle to more closely approximate the normal electrical activation that initiates in the superior, septal aspect of the left ventricle. However, as explained below, many lead-based systems cause an abnormal conduction pattern to propagate through the cardiac tissue because lead-based electrodes are limited to being placed at an abnormal site of origin.

One drawback of lead-based pacing systems is that they are not well suited for endocardial pacing in the left ventricle. For the emerging treatment of heart failure, through what is commonly known as resynchronization therapy, bi-ventricular pacing is utilized. Bi-ventricular pacing requires that an additional lead be placed in contact with the left ventricle. To access the left ventricle, a third lead is typically advanced through the right atrium and the orifice of the coronary sinus, and then the third lead is maneuvered through the coronary veins to a position in the vein that is on the epicardial aspect of the lateral wall of the left ventricle. Less commonly, the third lead is placed directly on the epicardium and then subcutaneously tunneled to the implant location of the pacing device. The left ventricle is accordingly stimulated epicardially from this position. Unlike normal endocardial electrical activation in which the activation initiates in the endocardium and then propagates through the myocardial layers to the epicardium, such epicardial stimulation of lead-based electrodes progresses in the opposite transmural direction. This approach may reduce the efficacy of lead-based left ventricular pacing. Moreover, because the size and course of the coronary sinus varies from patient to patient, it is often difficult to manipulate the lead within the coronary sinus. The available stimulation sites within the coronary sinus are accordingly limited by the individual anatomic features of each patient. Also, because the lead is located on the epicardial side of the left ventricle, the electrical current/energy required to stimulate the left ventricle is generally significantly higher for this treatment compared to standard endocardial locations within the right ventricle. This occurs, in part, because the electrical contacts of the lead may not be in intimate contact with the myocardium (i.e., they may be more preferentially in contact with the vein or situated centrally within the vessel). Thus, higher electrical currents in the stimulation pulse may be required to initiate activation. These higher electrical currents may stimulate other unintended, nearby structures such as the phrenic nerve.

Although implanting pacemaker leads directly within the left ventricle has been proposed, it is not yet practiced because prior art medical devices that reside on the arterial side (left side) of the cardiovascular system increase the risk of stroke, myocardial infarction, and vascular occlusions. For example, left ventricular lead placement is not practical because thrombus formation on the lead body and subsequent systemic embolization would require patients to have long-term anticoagulation drugs. Moreover, it may be necessary to extract the lead from the left ventricle, but this procedure may have considerable risks. Placing the lead retrograde through the aortic valve may cause aortic regurgitation and the proximate end of the lead may cause arterial bleeding because this end of the lead would need to exit through an artery. Alternatively, placing the lead through a transeptal atrial puncture and then across the mitral valve into the left ventricle, may possibly worsen mitral valve regurgitation. Therefore, implanting lead-based electrodes into the left ventricle of the patient is not practical using conventional systems.

Another aspect of implanting pacing systems is to determine the stimulation site to effectuate optimal synchronization timing between pacing sites and the resultant hemodynamic performance. Clinical studies of pacing modalities to treat heart failure have shown that acute hemodynamic measurements are correlated with patient benefit. For example, a separate catheter placed acutely within the left ventricle has been used to evaluate hemodynamic responses for bi-ventricular pacing. Specifically, a pressure-volume catheter system has been used to obtain simultaneous measurement of (a) aortic and left ventricular pressures, (b) an index of contractility ($dP/dT_{max}$), and/or (c) left ventricular chamber volumes. Based on these clinical studies, it appears that it would be desirable to optimize the number and location of the stimulation sites to provide the optimal patient benefit.

One drawback of using hemodynamic measurements within the left ventricle for pacing applications is that it is impractical to implant lead-based electrodes in the left ventricle for the reasons explained above. Therefore, even though hemodynamic responses have been evaluated for bi-ventricular pacing using epicaridal lead placements, this concept has not been used for endocardial pacing in the left ventricle because conventional pacing devices are not well suited for left ventricular pacing even if such left ventricular sites are the optimal stimulation sites.

BRIEF DESCRIPTION OF THE DRAWINGS

FIG. 1A is a side elevation view of an apparatus for determining an implantation site in accordance with an embodiment of the invention.

FIG. 1B is a cross-sectional view illustrating an embodiment of the implementation of the apparatus illustrated in FIG. 1A.

FIG. 2 is a side elevation view of an apparatus for determining an implantation site in accordance with another embodiment of the invention.

FIG. 3A is a side elevation view of a pressure-volume sensor for use in an apparatus for determining an implantation site in accordance with still another embodiment of the invention.

FIG. 3B is a side elevation view of a stimulation unit for use with the pressure-volume sensor of FIG. 3A in accordance with an embodiment of the invention.

FIG. 3C is a cross-sectional view illustrating an implementation of the device illustrated in FIGS. 3A and 3B.

DETAILED DESCRIPTION

A. Overview

Figure 4A:
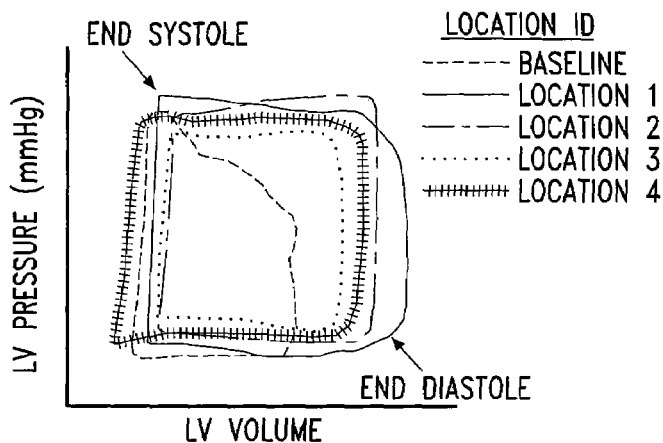
FIGS. 4A-4E are graphs illustrating various hemodynamic responses measured in accordance with embodiments of the invention.

The present invention is directed toward apparatus and methods for determining an implantation site for attaching a stimulation electrode to the heart of a patient. Many embodiments of the invention are directed toward implanting a leadless stimulation electrode that is configured to convert acoustic energy to electrical energy and deliver the electrical energy to the stimulation site. Suitable leadless stimulation electrode devices are disclosed in U.S. patent application Ser. Nos. 11/315,023; 11/315,524; 60/689,606; 60/639,037; 60/639,056; 60/704,620, entitled "Efficiently Delivering Acoustic Energy to Tissue," filed on Aug. 1, 2005; and 60/713,241, entitled "Methods And Systems for Heart Failure Treatments Using Ultrasound And Leadless Implantable Device," filed on Aug. 30, 2005, which are herein incorporated by reference. Because the stimulation electrodes are leadless, they can be placed in the left ventricle in a manner that enables pacing therapies that are not practical using lead-based electrodes.

One aspect of the invention is directed toward methods for determining an endocardial implantation site for implanting an electrode, such as a leadless stimulation electrode. This method includes delivering sufficient electrical energy for initiation of cardiac activation to a plurality of different test locations at the heart of a patient, and determining hemodynamic responses in reaction to the stimulus delivered to the different test locations. This method further includes identifying an implantation site for implanting the electrode by selecting at least one of the test locations corresponding to a favorable hemodynamic response.

Another embodiment of a method in accordance with the invention is directed toward determining an implantation site for implanting an electrode in the left ventricle of a patient. This method includes delivering sufficient electrical energy for initiation of cardiac activation to a plurality of different test locations within the left ventricle of the patient, and determining hemodynamic responses in reaction to the stimulus delivered to the different test locations. This method further includes identifying an implantation site for implanting the electrode by selecting at least one of the test locations within the left ventricle corresponding to a favorable hemodynamic response.

Another method of determining an implantation site for attaching a stimulation electrode in accordance with the invention comprises locating a leadless electrode at a first test location at the heart of the patient. The leadless electrode in this embodiment is configured to convert acoustic energy to electrical energy. This method continues by delivering sufficient electrical energy for initiation of cardiac activation to the first test location via the leadless electrode by wirelessly transmitting acoustic energy to the leadless electrode, and determining a first hemodynamic response in reaction to that stimulus to the first test location. This method further includes delivering sufficient electrical energy for initiation of cardiac activation to a second test location via the leadless electrode by wirelessly transmitting acoustic energy to the leadless electrode, and determining a second hemodynamic response in reaction to that stimulus to the second test location. After determining the first and second hemodynamic responses, this process can continue by delivering sufficient electrical energy for initiation of cardiac activation to the heart and determining the corresponding hemodynamic response at several different locations. This method further includes identifying an implantation site for implanting the leadless electrode by selecting at least one of the test locations corresponding to a favorable hemodynamic response.

Yet another method of automatically determining an implantation site for attaching a leadless stimulation electrode in accordance with an embodiment of the invention is directed toward a leadless electrode that is configured to convert acoustic energy to electrical energy and deliver the electrical energy to the stimulation site. An embodiment of this method comprises delivering sufficient electrical energy for initiation of cardiac activation to a plurality of different test locations at the heart of the patient, and determining hemodynamic responses in reaction to the stimulus delivered to the different test locations. This method further includes identifying an implantation site for implanting the electrode by operating a computer to automatically select at least one of the test locations corresponding to a favorable hemodynamic response.

Another aspect of the present invention is directed toward an apparatus for determining an implantation site for attaching a stimulation electrode to the heart of a patient. One embodiment of such an apparatus includes a catheter comprising an elongated body having a proximal portion and a distal portion configured to be inserted into the heart of the patient. The apparatus can further include a hemodynamic sensor and a stimulation electrode at the distal portion of the body. The stimulation electrode can comprise (a) a transducer configured to convert acoustic energy to electrical energy and (b) an electrical contact electrically coupled to the transducer to deliver sufficient electrical energy for initiation of cardiac activation from the transducer to the stimulation site.

Another aspect of the invention is directed toward systems for determining an implantation site for attaching a stimulation electrode to the heart of a patient. One embodiment of such a system comprises a generator configured to wirelessly transmit acoustic energy, a stimulation electrode configured to be placed in contact with the heart tissue of a patient, and a hemodynamic sensor. The stimulation electrode comprises (a) a case, (b) a transducer at least partially in the case and configured to convert the wirelessly transmitted acoustic energy from the generator to electrical energy, and (c) electrical contact electrically coupled to the transducer and configured to deliver the electrical energy from the transducer to the heart tissue of the patient. The hemodynamic sensor is configured to detect hemodynamic responses corresponding to the electrical energy delivered from the stimulation electrode to the heart of the patient. The stimulation electrode and the hemodynamic sensors can be attached to separate catheters such that they are independently positionable within the heart of the patient. In other embodiments, however, the stimulation electrode and the hemodynamic sensor are both carried by a single catheter or other type of elongated body that is configured to be positioned within the heart of the patient.

Another embodiment of a system in accordance with the invention comprises a generator configured to wirelessly transmit a source energy, a stimulation electrode configured to be placed in contact with the heart tissue of the patient, and a hemodynamic sensor. The stimulation electrode comprises a transducer configured to convert the source energy to electrical energy and an electrical contact configured to deliver the electrical energy to the heart of the patient. The hemodynamic sensor is configured to detect acute intrinsic hemodynamic responses in reaction to electrical energy applied to the heart by the stimulation electrode. This system can further include a computer operatively coupled to the hemodynamic sensor and the stimulation electrode. In one embodiment, the computer includes a computer-operable medium containing instructions that provide an output indicative of stimulation performance of the stimulation electrode at test sites of the heart of the patient. The computer-operable medium can further provide an output in which the stimulation performance of the stimulation electrode is mapped onto an image or other representation of the heart of the patient.

In several embodiments of the present invention, the generator is a controller-transmitter device that transmits ultrasound energy through the patient. The controller-transmitter device can be implanted in the patient, or the controller-transmitter device can be external to the patient. The leadless stimulation electrodes can be receiver-stimulator devices configured to be located at different locations throughout the endocardium of cardiac chambers of the patient. In general, at least one of the receiver-stimulator devices is configured to be in direct contact with the endocardial tissue. Suitable controller-transmitter devices and receiver-stimulator devices are disclosed in the U.S. patent applications incorporated by reference above.

In operation, the site for implanting a receiver-stimulator device is based on an assessment of cardiac performance from pacing at the site (such as, assessing the electrical activation timing, activation pattern, and/or hemodynamic responses). In many applications, the implantation site corresponds to the test location where the cardiac performance response indicates an optimal hemodynamic performance. The cardiac performance response can be assessed by measuring the pressure, volume, blood flow velocity, wall movement timing, and/or other hemodynamic measurements, and/or electrical activation timing or activation pattern mapping. These measurements are used to derive the parameters of cardiac performance such as ejection fraction, stroke volume, systolic blood pressure, arterial blood pressure, pressure change rate ($dP/dT_{max}$), valve pressure gradient, electrical activation sequences, electrical conduction times, and/or other cardiac performance parameters. According to this invention, the implantation site at the endocardium is determined by selecting the location corresponding to the desired or optimized cardiac performance parameters.

FIGS. 1A-7 illustrate several apparatus and methods for determining one or more implantation sites in accordance with selected embodiments of the invention. Although specific details of the invention are set forth in the following description and these figures, one skilled in the art will understand that the present invention will have additional embodiments, or that other embodiments of the invention may be practiced without several of the specific features explained in the following description. Where the context permits, singular or plural terms may also include the plural or singular term, respectively. Moreover, unless the word "or" is expressly limited to mean only a single item exclusive from other items in reference to a list of at least two items, then the use of "or" in such a list is to be interpreted as including (a) any single item in the list, (b) all of the items in the list, or (c) any combination of the items in the list. Additionally, the term "comprising" is used throughout to mean including at least the recited feature(s) such that any greater number of the same features and/or types of other features and components are not precluded.

B. Embodiments of Apparatus for Determining Implantation Sites

FIG. 1A is a side elevation view of an apparatus 1 for determining an implantation site for a stimulation electrode, and FIG. 1B is a cross-sectional view of an implementation of the apparatus 1 in the heart H of a patient. The apparatus 1 can include an elongated body, such as a steerable catheter 10, that is configured to be inserted into the heart H. The apparatus 1 can further include a stimulation element 20, and one or more hemodynamic sensors 30 (identified individually as first sensor 30a and second sensor 30b). Although two hemodynamic sensors 30 are illustrated in FIGS. 1A and 1B, any number of hemodynamic sensors 30 can be located along the length of the elongated body.

The catheter 10 can include a pull-wire (not shown) attached to the distal end and an actuator mechanism (not shown) at the proximal end attached to the pull-wire. The construction of the catheter 10 can be the same as catheters that are used for cardiac mapping, cardiac ablation, electrophysiology, and other types of cardiac procedures. As a result, the distal end of the catheter can be steered through the vasculature and the heart, and the catheter can be held at locations in the heart H such that the distal end of the catheter containing the stimulation element 20 contacts the endocardium.

The stimulation element 20 can be lead-based stimulation electrodes or a leadless electrode. In one embodiment of a leadless electrode, the stimulation element 20 comprises acoustic receiver-stimulator device having a case, a transducer at least partially in the case, and stimulation electrodes. The transducer can be a piezoelectric element or other device configured to convert wirelessly transmitted acoustic energy from a remote acoustic generator to electrical energy. The stimulation electrodes are electrically coupled to the transducer and configured to deliver the electrical energy from the transducer to the heart of the patient. In the embodiment illustrated in FIG. 1A, the stimulation element 20 is a small cylindrical or button-shaped component that can be fixed to the heart H with a screw-in helix element or other type of anchor 22. Alternately, the screw-in or other type of anchor 22 could function as the stimulation electrode. The apparatus 10 can further include a deployment mechanism 24 that releases the stimulation element 20 from the catheter 10. In operation, the deployment mechanism 24 is activated to detach the stimulation element 20 from the elongated body 10 after the anchor 22 has been secured to the patient to permanently implant the electrode in the patient. This aspect of the apparatus is particularly useful in embodiments in which the stimulation element 20 is a leadless electrode, such as one of the receiver-stimulator devices disclosed in the U.S. patent applications incorporated by reference above.

In an alternative embodiment, the apparatus 1 can have more than one stimulation element 20, or the stimulation element 20 can be lead-based stimulation electrodes having electrode wires running the length of the catheter 10. In yet another alternative embodiment, the catheter 10 is a pacemaker lead with pressure sensors adapted to be part of the lead construction.

In the embodiment illustrated in FIGS. 1A and 1B, the hemodynamic sensors 30 are side-facing transducers along a common side of the distal portion of the catheter 10. More specifically, the first hemodynamic sensor 30a is located along the distal portion to be positioned in the left ventricle LV of the heart H, and the second hemodynamic sensor 30b is located proximally of the first hemodynamic sensor 30a to be located in the ascending aorta. Other orientations and placement of the sensors, not shown, may also be envisioned including a transspetal approach with one or more pressure sensors in the left atrium. The configuration shown in FIGS. 1A and 1B of the first and second hemodynamic sensors 30a and 30b can measure local pressure changes from the left ventricle LV and the ascending aorta. The pressure gradient between the two locations can also be obtained. In several embodiments of the apparatus 1, the hemodynamic sensors 30 collect pressure data over time, and in particular embodiments these sensors collect diastolic and systolic pressures at the locations of these sensors. The pressure data collected by the sensors 30b is then processed in a computer and provided to a practitioner in a useful format.

The hemodynamic sensors 30 may be pressure transducers, flow rate meters, electrical sensors, or other types of sensors that can detect hemodynamic measurements. In one embodiment, the hemodynamic sensors are solid-state pressure transducers/sensors similar to those used on Millar Mikro-Tip catheters, or they may be any type of pressure sensor adapted for monitoring intravascular blood pressure. In the case of using solid-state pressure sensors, the apparatus 1 will further include wires running the length of the catheter 10 to electrically couple the sensors 30 to equipment outside of the patient. For example, the sensors 30 can be connected to external pressure recording and monitoring systems to obtain real time and post-process pressure data. Suitable external recording and monitoring systems include the BIO-PAC systems, MP 100.

FIG. 2 is a side elevation view of an alternative embodiment of an apparatus 100 in accordance with another embodiment of the invention. In this embodiment, the apparatus 100 includes an elongated body having a steerable sheath 110 and a non-steerable catheter 112 received in the steerable sheath 110. The apparatus 100 further includes a stimulation element 20 at a distal portion of the non-steerable catheter 112 and one or more hemodynamic sensors 30 on the side of the sheath 110. The physician manipulates the sheath 110 to move the non-steerable catheter 112 through the patient until the stimulation element 20 contacts an endocardial location. Similar to the embodiments discussed above with reference to FIGS. 1A and 1B, the non-steerable catheter 112 can include lead-based stimulation electrodes or a leadless electrode for electrically stimulating the endocardium. The apparatus 100 is expected to operate in a manner similar to that of the apparatus 1 illustrated in FIGS. 1A and 1B.

Referring to FIG. 1B, the apparatus 1 or the apparatus 100 is inserted through the aorta and into the heart H such that the stimulation element 20 is placed against a first test location $L_1$ at the endocardium of the left ventricle LV. The first hemodynamic sensor 30a can be within the left ventricle and the second hemodynamic sensor 30b can be in the ascending aorta as explained above. At this point, sufficient electrical energy for initiation of cardiac activation as a paced rhythm is delivered to the first test location $L_1$ via the stimulation element 20, and the hemodynamic sensors 30a and 30b measure the acute intrinsic hemodynamic response in reaction to the stimulus delivered. After recording the hemodynamic response, the catheter 10 is manipulated to position the stimulation element 20 at another test location $L_n$ and sufficient electrical energy for initiation of cardiac activation as a paced rhythm is delivered to the subsequent test location $L_n$ via the stimulation element 20. The hemodynamic sensors 30a and 30b accordingly monitor the hemodynamic response in reaction to the stimulus delivered to the subsequent test location $L_n$. This procedure can be repeated several times at several different test locations.

In a particular application, the process of using the apparatus 1 to measure the hemodynamic response at a plurality of test locations begins by determining a baseline for the patient. For example, when the stimulation element 20 is placed at one of the endocardial test locations in the left ventricle LV, the baseline pressure data from the hemodynamic sensors is collected, recorded and analyzed over one or more cardiac cycles without applying electrical energy to the test site. This baseline data is typically obtained during the intrinsic rhythm of the heart H. If the patient has a very slow intrinsic heart rate that requires constant pacing with a pacemaker, the implanted pacing leads of the pacemaker or the temporary leads of the external pacemaker can be used to establish a baseline pacing rate to substitute for the intrinsic rhythm. The baseline value can also be compared with other measurements during the intrinsic or paced rhythm. For example, the baseline value from the sensors 30 can be compared with the heart rate, presence or absence of atrial ventricular synchrony, presence or absence of underlying arrhythmias, or blood pressure taken from an arm pressure cuff.

After determining the baseline value, sufficient electrical energy for initiation of cardiac activation is applied to the test location via the stimulation element 20 to initiate a cardiac-paced rhythm. After the characteristics of the hemodynamic data have been captured during the paced rhythm at one test location, the stimulation element 20 is moved to a new test location in the heart H and sufficient electrical energy for initiation of cardiac activation is applied to the new test location via the stimulation element 20 to initiate another cardiac-paced rhythm from the new test location. The hemodynamic data and the location of the new test site are accordingly collected and recorded during the paced rhythm for the new test location. This process is repeated for any number of selected test locations in the left ventricle LV endocardium or other locations of the heart H.

In some embodiments, the duration of the paced rhythm may be varied to determine the hemodynamic responses to different heart rates. Also, the A-V interval may need to be controlled to maintain A-V synchrony or may need to be varied to determine the A-V interval to optimize the atrial contribution to ventricular filling. These judgments can be implemented by an attending physician analyzing the data gathered during the process.

The hemodynamic data, such as pressure data, can be processed to provide one or more hemodynamic parameters to a practitioner or a computer. Suitable hemodynamic parameters include the rate of pressure change (e.g., positive $dP/dT_{max}$, negative $dP/dT_{max}$, or $dP/dT_{min}$), peak systolic pressure, peak diastolic pressure, end diastolic pressure, end systolic pressure, atrial pulse pressure, left ventricle LV pressure wave forms, aortic pressure wave forms, ejection period, aortic valve pressure gradient, and other parameters. Similar hemodynamic measurements can be obtained non-invasively using an echocardiographic imaging system. Echocardiographic data could be obtained for each test stimulation location during implant testing, or supplemental data could be obtained before the implant procedure. In all cases, the desired implantation site can be selected by comparing the hemodynamic parameters and/or the hemodynamic data corresponding to the individual test sites. In one embodiment, the desired implantation site corresponds to the location where the greatest improvement in hemodynamic status occurs based upon a comparison of the hemodynamic baseline and the hemodynamic parameters corresponding to the various test locations. In a further embodiment, the implantation site can be confirmed by placing the stimulation element 20 back at the selected location and repeating the sequence to determine whether the test location produces the expected result.

The test location and the corresponding hemodynamic response from the sensors can be referenced with diagrams or real images (fluoroscopic, ultrasound, MRI, CT, etc.) of the patient's anatomy to map or otherwise correlate the hemodynamic responses to the patient's anatomy. For example, the correlation may be done using an EP mapping system that contains three-dimensional localization technology. Suitable EP mapping systems can be the ultrasound ranging system provided by Boston Scientific, Inc., the impedance ranging system provided by Endocardial Solutions, and/or the magnetic tracking system provided by Biosense Webster. These and other systems can record catheter positions so that the operator can return the catheter to stored locations. These and other systems can also record electrical activation data such as conduction times between two locations or illustrate conduction patterns, known as maps. Thus by using the stimulation electrodes as electrogram recording electrodes in EP systems, electrical conduction data is also available to correlate a test site with improved cardiac performance. Required elements that enable these mapping technologies may be incorporated into the catheter embodiments discussed within but are not shown.

After selecting an implantation site for implanting a stimulation electrode, a suitable stimulation electrode is implanted at that location. In one embodiment, the stimulation element 20 is an acoustic stimulation electrode such as the receiver-stimulator electrode described above, and the stimulation element 20 is detached from the catheter 1 and fixed to the heart H whereupon the catheter 1 is withdrawn/removed. In another embodiment, the catheter 1 itself is fixed to the tissue and used as a pacemaker lead.

FIGS. 3A-3C illustrate an apparatus 200 for determining an implantation site for attaching a stimulation electrode to the heart of a patient in accordance with another embodiment of the invention. The apparatus 200 includes a pressure-volume catheter 210 (FIG. 3A) and a stimulation catheter 212 (FIG. 3B). The pressure-volume catheter 210 and the stimulation catheter 212 operate simultaneously within the heart H (FIG. 3C) to stimulate endocardial test locations and measure the hemodynamic responses corresponding to the various test locations.

Referring to FIG. 3A, the illustrated embodiment of the pressure-volume catheter 210 includes an elongated body 211 having a distal portion with a pigtail segment 213. The pressure-volume catheter 210 further includes a plurality of first hemodynamic sensors 230 (identified individually by reference numbers 230a and 230b) and a plurality of second hemodynamic sensors 240. The first hemodynamic sensors 230 can be pressure sensors, and the second hemodynamic sensors 240 can be electrical sensors (e.g., ring electrodes). The first hemodynamic sensors 230 can accordingly collect pressure data as explained above with respect to FIGS. 1A-2. The second hemodynamic sensors 240 can electrically determine the blood volume within the left ventricle LV using conductance techniques known in the art. For example, an electrical current can be delivered between the distal-most sensor 240 and the proximal-most sensor 240 in the left ventricle LV chamber, and the electrical conductivity of the blood within the chamber can be measured at each of the intermediate second sensors 240. By monitoring the electrical conductivity of the blood over a cardiac cycle, the volume of blood in the left ventricle LV can be determined at different times in the cardiac cycle using standard conductance/volume relationships known in the art. When the pressure data from the first hemodynamic sensors 230 is combined with the volume data from the second hemodynamic sensors 240 over a cardiac cycle, the data can be represented in what is commonly known as a pressure-volume loop.

Referring to FIG. 3B, the stimulation catheter 212 can include an elongated body 214 and the stimulation element 20 described above. The stimulation catheter 212 can accordingly be similar to any of the embodiments of the apparatus 1 and/or 100 described above. The stimulation element 20 attached to the elongated body 214 can be a conventional wired electrode or an acoustic receiver-stimulator device in several embodiments of the stimulation catheter 212.

Referring to FIG. 3C, the stimulation catheter 212 is positioned in the left ventricle LV such that the stimulation element 20 is placed in contact with the heart tissue at one or more endocardial test locations. The pressure-volume catheter 210 is also positioned in the left ventricle LV. The pressure-volume catheter 210 collects pressure-volume data to measure the hemodynamic responses corresponding to the stimulation provided by the stimulation catheter 212 at the various test locations. More specifically, the pressure/volume data is collected, recorded, and analyzed by a signal processing system for one or more cardiac cycles during (a) the intrinsic rhythm of the heart and (b) a paced rhythm in which electrical energy is delivered to the heart via the stimulation element 20. Although the stimulation catheter 212 is repositioned within the left ventricle LV to place the stimulation element 20 at a plurality of different test locations, the pressure-volume catheter 210 may remain in the same position to collect the pressure-volume data. As explained above, the data obtained by the pressure-volume catheter 210 can be correlated with the particular test locations of the stimulation element 20 to determine the desired implantation site for a permanently implanted stimulation electrode.

Figure 4B:
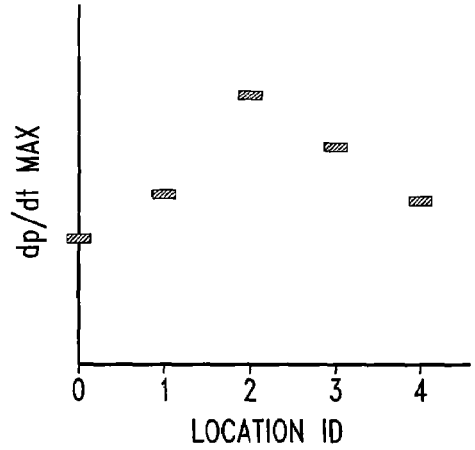
Figure 4C:
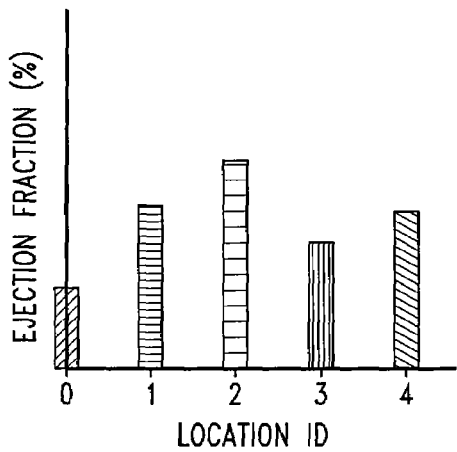
Figure 4D:
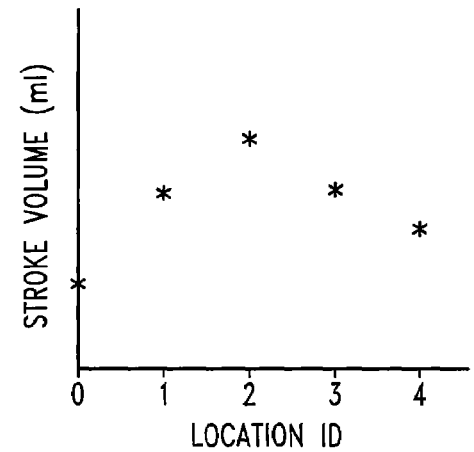
Figure 4E:
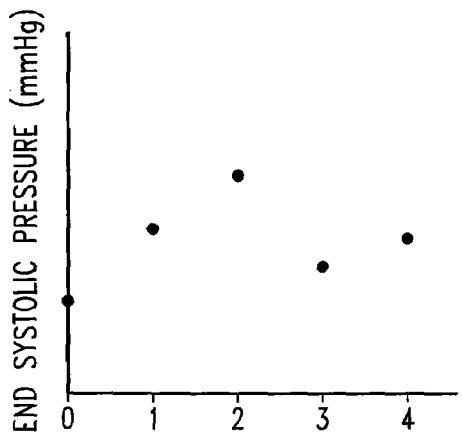

FIGS. 4A-4E are a plurality of graphs illustrating a variety of relationships for comparing hemodynamic volume and pressure parameters. The graphs illustrated in FIGS. 4A-4E are examples representing hemodynamic data to visualize the differences between the test locations. FIG. 4A illustrates a plurality of pressure-volume loops corresponding to the baseline (e.g., location 0) and four test locations (e.g., locations 14). In many applications, the selected stimulation location will correspond to the location having the largest pressure-volume loop (e.g., maximum area). FIG. 4B is a graph illustrating the rate of pressure change at the baseline and at test locations. In this embodiment, the stimulation site is generally selected to correspond to the site having the maximum rate of pressure change (e.g., maximum flow rate). FIG. 4C is a bar graph illustrating the ejection fraction for the baseline and at test locations. In this embodiment, the selected implantation site generally corresponds to the location having the maximum ejection percentage. FIG. 4D is a graph illustrating the stroke volume at the baseline and at test locations. In this embodiment, the selected implantation location generally corresponds to the location having the maximum stroke volume. FIG. 4E is a graph illustrating the end-systolic pressure at the baseline and at test locations. In several embodiments, the selected stimulation site corresponds to the location having the maximum end systolic pressure.

Figure 5:
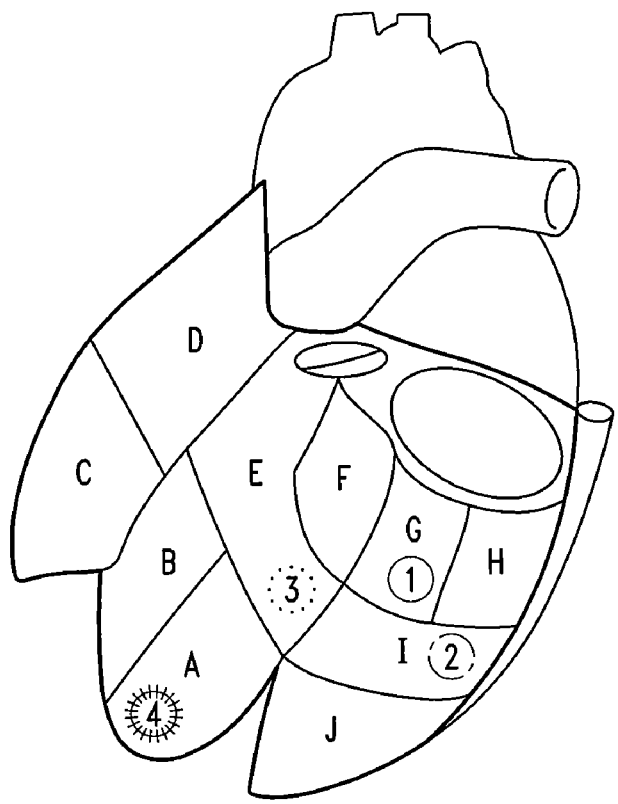
FIG. 5 is a schematic diagram illustrating a representation of a heart and an output indicative of stimulation performance.

FIG. 5 is a representation of the heart of the patient. In one embodiment, the representation can be adapted from the Josephson "Clinical Cardiac Electrophysiology-Techniques and Interpretation," and is a perspective view of the left ventricle open at the lateral wall with the anterior wall to the right of the figure. A variety of sections of the left ventricle are labeled, and the test locations (e.g., locations 14) are referenced or otherwise mapped onto the representation or alternatively onto other virtual representations including 3D localization technologies. In other embodiments, actual images of the heart H of the patient obtained using fluoroscopy, ultrasound, MRI, or other imaging techniques can be used to provide a representation of the patient's heart upon which the test locations can be mapped.

The foregoing apparatus and methods described above with reference to FIGS. 1A-5 can also be applied in other chambers of the heart. Additionally, other embodiments in accordance with the invention may be repeated using multiple catheters and/or multiple stimulation electrodes in a variety of locations between chambers or within the same chamber. Other embodiments can adjust the timing and stimulation sequence between stimulator elements, and/or multiple locations may be selected for test locations for either simultaneous or sequential stimulation. Additionally, other embodiments of the invention include any similar variation of the methods and apparatus that involve using hemodynamic data to optimize the delivery of pacing stimulation. As an example, after obtaining the intrinsic rhythm, a permanent conventional pacing lead or a leadless stimulation lead that converts acoustic energy to electrical energy may first be implanted in the right ventricle. The method could then stimulate locations in the left ventricle as described above. The hemodynamic data could accordingly be collected in a bi-ventricular paced rhythm with different locations of the stimulation elements 20. As another example, a patient may have a pre-existing pacemaker with conventional right atrial and right ventricle leads. Baseline data would first be obtained in the conventional dual-paced rhythm, and then a device similar to the stimulation catheter 212 that has a stimulation element 20 at its distal end would then be placed in the left ventricle. The hemodynamic data would then be collected in the bi-ventricular paced rhythm with different stimulation locations. As another example, the pressure-volume catheter 210 can include a stimulation element 20 attached to the elongated body 211 as shown in broken lines in FIG. 3A.

The foregoing embodiments of apparatus and methods in large part describe aspects of hemodynamic measurements that can be made within the heart. Additionally, other embodiments in accordance with the invention may use non-invasive methods of measuring hemodynamic responses. For example, the use of transthoracic ultrasound imaging can be used to measure and characterize heart wall motion timing, wall motion velocity, wall motion force, chamber volume, ejection fraction, flow velocity, and the like. Further the use of blood pressure cuffs on the arms or other extremities would provide hemodynamic measurement of pressure changes as a response to pacing site selection.

The foregoing embodiments of apparatus and methods provide advantages for implantation of cardiac pacing electrodes by using hemodynamic optimization for both single- or multi-site endocardial pacing. There are many potential locations to implant electrodes, and in particular the leadless receiver-stimulator devices that convert acoustic energy to electrical energy can be implanted in places where it is not practical to implant lead-based electrodes. Several embodiments of the apparatus and methods are expected to determine efficacious stimulation sites by using leadless electrodes to take advantage of stimulation sites that are not practical for lead-based electrodes (e.g., endocardial left ventricle locations). As a result, one advantage of particular embodiments of the invention is that the combination of using hemodynamic parameters for implanting leadless electrodes at endocardial left ventricle sites is expected to improve left ventricle function compared to conventional techniques.

In specific embodiments of the co-pending disclosures incorporated by reference above, the hemodynamic data may be used in situations in which the ideal locations for the controller-transmitter are limited due to anatomic constraints. The ideal location for the controller-transmitter device is where it can deliver the maximum amount of acoustic energy to the leadless stimulation electrodes, but certain physiological constraints by the thoracic region and the lungs may limit the locations for implanting the controller-transmitter. Therefore, optimization of the implant locations for the controller-transmitter and the receiver-stimulator devices may require testing at different sites for both the controller-transmitter and the receiver-stimulator devices to obtain the highest level of hemodynamic improvement.

C. Embodiments of Methods for Determining Implantation Sites

Figure 6:
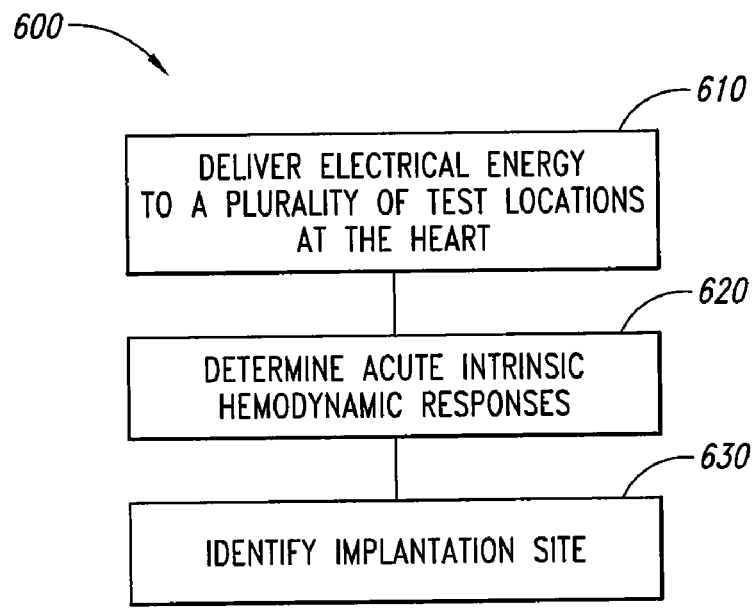
FIG. 6 is a flow chart illustrating a method in accordance with an embodiment of the invention.

FIG. 6 is a flow chart illustrating a method 600 of determining an implantation site for attaching a stimulation electrode to the heart of a patient in accordance with one embodiment of the invention. The stimulation electrode, for example, can be a leadless electrode configured to convert acoustic energy to electrical energy and deliver the electrical energy to the stimulation site. The method 600 can include a delivering stage 610 comprising delivering sufficient electrical energy for initiation of cardiac activation to a plurality of different test locations at the heart of the patient. As described above, the electrical energy can be delivered to the endocardium of a chamber in the heart using a lead-based electrode or a leadless electrode. In a specific example, the electrical energy is delivered to a plurality of different test locations within the left ventricle of the heart.

The method 600 further includes a sensing stage 620 comprising determining acute intrinsic hemodynamic responses in reaction to the stimulus to the different test locations. As described above, the sensing stage 620 provides the hemodynamic data corresponding to each test location. The method 600 further includes an identification stage 630 comprising identifying an implantation site for implanting the electrode by selecting at least one of the test locations that corresponds to a favorable hemodynamic response. As described above with reference to FIGS. 4A-5, the particular hemodynamic response can be one or more of several hemodynamic parameters that indicate the desired result of providing the stimulation to the heart.

Figure 7:
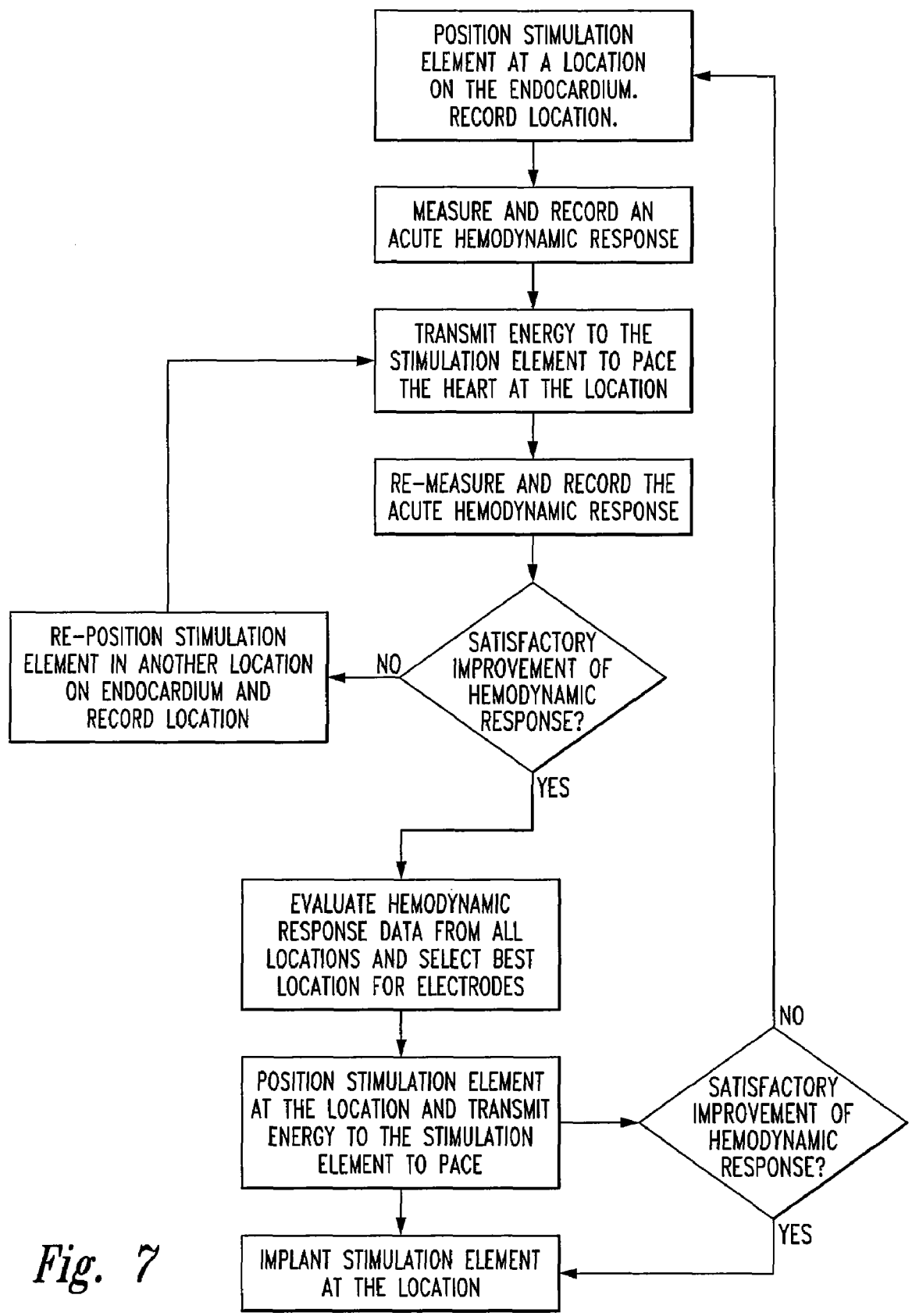
FIG. 7 is a flow chart illustrating a method in accordance with another embodiment of the invention.

FIG. 7 is a graph illustrating another embodiment of the invention. For example, the process for collecting and analyzing acute hemodynamic data to select endocardial locations for the method 600 is further defined in the embodiment illustrated in FIG. 7.

From the foregoing, it will be appreciated that specific embodiments of the invention have been described herein for purposes of illustration, but that various modifications may be made without deviating from the spirit and scope of the invention. Accordingly, the invention is not limited except as by the appended claims.

We claim:

1. A method of implanting a stimulation electrode within the heart of a patient, comprising:
    (a) positioning the stimulation electrode at a test location in the heart of a patient;
    (b) delivering electrical energy to the location;
    (c) determining a first acute hemodynamic response in reaction to the electrical energy delivered to the location;
    (d) assessing whether the first acute hemodynamic response is satisfactory;
    (e) repeating steps (a) through (d) until the first acute hemodynamic response at the test location is satisfactory;
    (f) delivering electrical energy to the test location;
    (g) determining a second acute hemodynamic response in reaction to the electrical energy delivered to the test location;
    (h) determining whether the second acute hemodynamic response is satisfactory;
    (i) repeating steps (a) through (h) until the test location that yields a satisfactory second acute hemodynamic response is identified; and
    (j) implanting the electrode at the identified site.

2. The method of claim 1 wherein the test locations are in the endocardial aspect of the left ventricle of the heart.

3. The method of claim 1, further comprising pacing the heart by wirelessly transmitting acoustic energy from an acoustic generator located remotely from the heart to the implanted leadless electrode, wherein the implanted leadless electrode converts the acoustic energy to electrical energy and applies the electrical energy to the identified site.

4. The method of claim 1 wherein determining the first and second acute hemodynamic responses comprises measuring pressure within a chamber of the heart.

5. The method of claim 1 wherein determining the first and second acute hemodynamic responses comprises measuring pressure from a first location within the left ventricle chamber of the heart and a second location within the ascending aorta.

6. The method of claim 1 wherein determining the first and second acute hemodynamic responses comprises measuring (a) pressure from a first location within the left ventricle of the heart and a second location within the ascending aorta, and (b) blood volume in the left ventricle.

7. The method of claim 1, wherein the electrical energy is delivered in step (b) using a lead wire.

8. The method of claim 7, wherein the stimulation electrode is leadless, the leadless stimulation electrode has an acoustic transducer configured to convert acoustic energy to electrical energy, the leadless stimulation electrode is configured to deliver the electrical energy converted by the acoustic transducer to the test location, and the delivering of step (f) uses wireless transmission of acoustic energy to the leadless stimulation electrode.

9. The method of claim 8 further comprising:
    determining acute hemodynamic responses in reaction to the electrical energy delivered via the lead wire and in reaction to the electrical energy converted by the acoustic transducer and delivered to the test locations; and
    identifying the site for implanting the electrode by operating a computer.

10. The method of claim 9 wherein:
    determining acute hemodynamic responses comprises ascertaining at least one hemodynamic parameter selected from at least one of a pressure- volume loop, rate of pressure change, ejection fraction, stroke volume, end systolic pressure, blood motion velocity, cardiac wall motion velocity, cardiac wall motion force, and cardiac wall motion timing for the test locations based on the determined hemodynamic responses; and
    identifying the site by operating the computer comprises selecting a test location corresponding to a value of the selected hemodynamic parameter.

11. The method of claim 1 wherein determining the first and second acute hemodynamic responses comprises measuring electrical activation timing within the heart.

* * * * *

UNITED STATES PATENT AND TRADEMARK OFFICE
CERTIFICATE OF CORRECTION

PATENT NO. : 7,702,392 B2 Page 1 of 1
APPLICATION NO. : 11/351569
DATED : April 20, 2010
INVENTOR(S) : Debra Echt et al.

It is certified that error appears in the above-identified patent and that said Letters Patent is hereby corrected as shown below:

Title Page, Item [57] Abstract, line 7, "that the" to read as --the--

Title Page, Page 2, Item [56] column 2, Other Publications, line 14, "Septa!" to read as --Septal--

Column 3, line 26, "epicaridal" to read as --epicardial--

Column 7, line 54, "transspetal" to read as --transseptal--

Column 14, line 6, Claim 3, "implanted leadless electrode, wherein the implanted leadless electrode" to read as --implanted electrode, wherein the implanted electrode--

Column 14, line 41 Claim 10, "pressure- volume" to read as --pressure-volume--

Signed and Sealed this

Thirty-first Day of August, 2010

David J. Kappos
*Director of the United States Patent and Trademark Office*